United States Patent [19]

Dubash et al.

[11] 4,383,986

[45] May 17, 1983

[54] HEMORRHOIDAL COMPOSITIONS

[75] Inventors: Darius D. Dubash, Somerville; Leonard L. Kaplan, East Brunswick; George A. Ziets, Flemington, all of N.J.

[73] Assignee: Ortho Pharmaceutical Corporation, Raritan, N.J.

[21] Appl. No.: 293,538

[22] Filed: Aug. 17, 1981

[51] Int. Cl.$^3$ .................. A61K 9/26; A61K 9/70; A61K 31/74; A61K 31/79
[52] U.S. Cl. ........................... 424/25; 424/28; 424/78; 424/80; 424/195; 424/240
[58] Field of Search ............... 424/80, 195, 25, 28, 424/78, 240

[56] References Cited

U.S. PATENT DOCUMENTS

| 2,880,130 | 3/1959 | Johnson | 167/65 |
| 3,264,188 | 8/1956 | Gresham | 167/84 |
| 3,287,222 | 11/1966 | Larde et al. | 167/84 |
| 3,343,540 | 9/1967 | Siegel | 128/269 |
| 3,440,320 | 4/1969 | Sacklet et al. | 424/230 |
| 3,899,580 | 8/1975 | O'Neill et al. | 424/241 |

FOREIGN PATENT DOCUMENTS 376221 8/1932 United Kingdom .

*Primary Examiner*—Donald B. Moyer
*Attorney, Agent, or Firm*—Benjamin F. Lambert

[57] ABSTRACT

An antipruritic, astringent and anti-inflammatory composition is provided. The composition is useful in the treatment of hemorrhoid symptoms.

21 Claims, No Drawings

HEMORRHOIDAL COMPOSITIONS

The present invention relates to a method of treating the symptoms of hemorrhoids. More specifically, the invention relates to a method of treating the symptoms of hemorrhoids by the application of an anti-inflammatory, antipruritic, astringent composition to the affected area. All three pharmacologic effects are provided in a single composition which is capable of delivering the active ingredients in a biologically effective state to the external hemorrhoidal tissue.

Hemorrhoids or piles result from a varicose condition of the external hemorrhoidal veins which causes painful swellings at the anus. When the dilated veins form tumors to the outer side of the external sphincter, or are covered by the skin of the anal canal, the condition is called external hemorrhoids; when the swollen veins are beneath the mucous membrane within the sphincter it is called internal hemorrhoids. The condition is often accompanied by bleeding, itching, burning and soreness.

Current preparations generally used to treat hemorrhoid symptoms involve the use of ointments, creams and suppositories that provide traditional medicinal ingredients such as local anesthetics, vasoconstrictors, antiseptics and emollient protectants. Medicated pads are also employed but these provide only mild astringent and antiseptic actions.

Four types of drugs are currently used to alleviate hemorrhoid symptoms: anesthetics, astringents, anti-inflammatory agents and lubricant softeners. The anesthetic is used to relieve the pain and itching of hemorrhoids. The astringent is used to contract, or draw together, the swollen tissues while the antiseptic is used to prevent infection. The lubricant softener is added to the product base to make it a more nonirritating vehicle. These drugs are available in many dosage forms. For intrarectal use, suppositories, creams, ointments, gels and foams are used along with applicators. Creams, ointments, gels, pads, liquids and foams are used externally. Some of the available products used for treating hemorrhoid symptoms contain one or two of these drugs but none of the available formulations combines all four effects in a biologically available form. Part of the problem is due to the fact that the bioavailability of drugs from anorectal dosage forms is a result of complex interplay among physiochemical, physiological, manufacturing, dosage form, dosage and application variables. Absorption from anorectal dosage forms involves release of the drug from the vehicle, dissolution into the surrounding medium, diffusion to a membrane and penetration of the membranes. Steroids have been employed in anorectal dosage formulations but the bioavailability of the drug is limited by the relative insolubility of steroids.

One object of the present invention is to provide a method of treating the symptoms of hemorrhoids.

A further object of this invention is to provide an anorectal dosage form which offers the sufferer of external hemorrhoids biologically active anti-inflammatory, antipruritic and astringent pharmacologic activity to relieve the disease state and the symptoms.

Applicants' invention is based upon the discovery that hydrocortisone dissolves in a solvent mixture of dimethyl isosorbide and an alcohol to form a stable solution. The solution is compatible with hamamelis extract, commonly known as witch hazel, and the resulting solvent mixture forms a biologically active solution from which the drug is readily available for quick absorption at the site of application. The solution is then absorbed on a suitable carrier in superwetted condition and when applied to the inflamed hemorrhoidal tissues, the superwetted carrier preferentially releases the hydrocortisone to provide anti-inflammatory and antipruritic activity while the hamamelis extract solution provides the astringent action. The superwetted state is achieved by the incorporation of an amphoteric surfactant into the liquid portion of the composition. This combination of ingredients provides, for the first time, a unique composition which offers four necessary pharmacologic actions for external hemorrhoid treatment in a biologically active system.

The composition of this invention is comprised of hydrocortisone dissolved in a liquid solution containing dimethyl isosorbide, an alcohol, hamamelis extract, a fungicide-bactericide, a film-former, an amphoteric surfactant and water.

Therapeutically effective amounts of hydrocortisone are employed in the formulation. Generally, amounts in the range of about 0.001 to 0.5 percent by weight have been found to be effective. The dimethyl isosorbide is present in an amount ranging from about 0.5–25 percent by weight. The preferred range is from about 15–25 percent. As the alcohol component alcohols such as propylene glycol, isopropyl alcohol, polyethylene glycol-400 or ethyl alcohol (190 proof) may be employed. The alcohol is present in the formulation in an amount ranging from about 0.5–15 percent by weight. The preferred range is about 5–15 percent. The hamamelis extract (86.0% witch hazel extract - 14% alcohol) is present in the solution in amounts ranging from about 43.0 to 58.45 percent by weight.

Methyl paraben can be employed as the fungicide-bactericide in the formulation. It may be present in an amount ranging from about 0.1–0.25 percent by weight; the preferred amount is 0.25 percent. Other materials which can be employed include the propyl and butyl parabens; cations like benzalkonium chloride and cetyl pyridinium chloride; phenyl mercuric chloride, phenol and derivatives of phenol such as resorcinol.

Film-formers such as polyvinylpyrrolidone having a molecular weight between 38,000 and 40,000, polymer JR-400 (a cationic cellulosic resin sold by Union Carbide having an approximate molecular weight of 400,000), sodium carboxymethyl cellulose and polyvinyl alcohol having a molecular weight between 170,000 and 250,000 may also be employed in the formulation. The film-former may be present in an amount ranging from about 0.075–1.375 percent by weight. The preferred range is from about 0.075–1.00 percent by weight.

As the amphoteric surfactant Miranol C2M-SF Conc., also known as Amphoteric 2 (an essentially salt-free, aqueous, amphoteric surfactant solution derived from coconut fatty acid manufactured by Miranol Chemical Co.) may be employed in concentrations ranging from about 0.1–0.25 percent by weight. The preferred concentration is about 0.25 percent. Other amphoteric surfactants which can be employed include Miranol 2MCA modified (Amphoteric 6—an aqueous salt solution derived from coconut fatty acid); Miranol CM Conc. (Amphoteric 1—an aqueous surfactant solution derived from coconut fatty acid); Miranol MHT (Amphoteric 17—an aqueous salt solution derived from lauric acid); Mirataine CB (an aqueous solution of cocamidoalkyl betaine); Mirataine BB (an aqueous solution of the lauric-myristic amidopropylbetaine) and Mirataine CDMB (an aqueous solution of N-cocoyl-N,N-dimethyl-glycine). The preferred surfactant, however, is Miranol C2M-SF Conc. The remainder of the composition (100% by weight) is water, preferably purified water which serves both as a vehicle for the formulation and a means of further diluting the preparation so as to avoid unnecessary irritation.

Any suitable means may be employed to apply the formulation to the affected areas. The solution can be applied by means of a sponge or commercially available nonwoven materials. Cotton swabs, absorbent wipes, pads and the like or any other absorbent material may also be employed. Care should be taken to use a sterile applicator in order to avoid infection.

The novel compositions can be prepared generally as follows:

The alcohol and the dimethyl isosorbide are thoroughly mixed and the hydrocortisone and methyl paraben are added to the mixture followed by the addition of the surfactant. The film-former is then dissolved in water and the aqueous solution is mixed well with the hamamelis extract. The solution containing the steroid is then added slowly to the solution of the film-former and the hamamelis extract with stirring. When either sodium carboxymethyl cellulose or polyvinyl alcohol is employed as the film-former, it is added to the solution containing the steroid prior to the addition of the aqueous solution in order to obtain a more homogeneous solution.

The following examples illustrate the invention and should not be construed as a limitation thereof:

EXAMPLE 1

|  | %/w/w |
|---|---|
| hydrocortisone | 0.50 |
| methyl paraben | 0.25 |
| polyvinylpyrrolidone | 1.00 |
| dimethyl isosorbide | 15.00 |
| propylene glycol | 15.00 |
| Miranol C2M-SF Conc. | 0.25 |
| witch hazel extract (86% solution) | 50.00 |
| purified water | 18.00 |
|  | 100.00g |

EXAMPLE 2

|  | %/w/w |
|---|---|
| hydrocortisone | 0.50 |
| dimethyl isosorbide | 15.00 |
| propylene glycol | 10.00 |
| alcohol (190 proof) | 5.00 |
| Miranol C2M-SF Conc. | 0.25 |
| methyl paraben | 0.25 |
| witch hazel extract | 50.00 |
| polyvinyl alcohol | 0.25 |
| purified water | 18.75 |
|  | 100.00 |

EXAMPLE 3

|  | %/w/w |
|---|---|
| hydrocortisone | 0.50 |
| dimethyl isosorbide | 15.00 |
| propylene glycol | 5.00 |
| alcohol (190 proof) | 10.00 |
| Miranol C2M-SF Conc. | 0.25 |
| methyl paraben | 0.25 |
| polyvinyl alcohol | 0.25 |
| witch hazel extract | 50.00 |
| purified water | 18.75 |
|  | 100.00 |

EXAMPLE 4

|  | %/w/w |
|---|---|
| hydrocortisone | 0.50 |
| methyl paraben | 0.25 |
| sodium carboxymethyl cellulose | 0.25 |
| dimethyl isosorbide | 15.00 |
| propylene glycol | 10.00 |
| alcohol (190 proof) | 5.00 |
| Miranol C2M-SF Conc. | 0.25 |
| witch hazel extract | 50.00 |
| purified water | 18.75 |
|  | 100.00 |

EXAMPLE 5

|  | %/w/w |
|---|---|
| hydrocortisone | 0.50 |
| methyl paraben | 0.25 |
| polyvinyl alcohol | 0.25 |
| dimethyl isosorbide | 15.00 |
| propylene glycol | 15.00 |
| Miranol C2M-SF Conc. | 0.25 |
| witch hazel extract | 50.00 |
| purified water | 18.75 |
|  | 100.00 |

EXAMPLE 6

|  | %/w/w |
|---|---|
| hydrocortisone | 0.50 |
| methyl paraben | 0.25 |
| polymer JR-400 | 0.25 |
| dimethyl isosorbide | 15.00 |
| propylene glycol | 10.00 |
| alcohol (190 proof) | 5.00 |
| Miranol C2M-SF Conc. | 0.25 |
| witch hazel extract | 50.00 |
| purified water | 18.75 |
|  | 100.00 |

EXAMPLE 7

|  | %/w/w |
|---|---|
| hydrocortisone | 0.50 |
| methyl paraben | 0.25 |
| polymer JR-400 | 0.25 |
| dimethyl isosorbide | 15.00 |
| propylene glycol | 5.00 |
| alcohol (190 proof) | 10.00 |
| Miranol C2M-SF Conc. | 0.25 |
| witch hazel extract | 50.00 |
| purified water | 18.75 |
|  | 100.00 |

EXAMPLE 8

| | %/w/w |
|---|---|
| hydrocortisone | 0.50 |
| dimethyl isosorbide | 15.00 |
| propylene glycol | 10.00 |
| PEG-400 (polyethylene glycol) | 5.00 |
| polyvinylpyrrolidone (K$_{32}$$^{29}$) | 1.00 |
| Miranol C2M-SF Conc. | 0.25 |
| methyl paraben | 0.25 |
| witch hazel extract | 50.00 |
| purified water | 18.00 |
| | 100.00 |

EXAMPLE 9

| | %/w/w |
|---|---|
| hydrocortisone | 0.50 |
| dimethyl isosorbide | 15.00 |
| propylene glycol | 10.00 |
| alcohol (190 proof) | 5.00 |
| polyvinylpyrrolidone (K$_{32}$$^{29}$) | 1.00 |
| Miranol C2M-SF Conc. | 0.25 |
| methyl paraben | 0.25 |
| witch hazel extract | 50.00 |
| purified water | 18.00 |
| | 100.00 |

EXAMPLE 10

| | %/w/w |
|---|---|
| hydrocortisone | 0.50 |
| dimethyl isosorbide | 15.00 |
| propylene glycol | 5.00 |
| alcohol (190 proof) | 10.00 |
| Miranol C2M-SF Conc. | 0.25 |
| polyvinylpyrrolidone (K$_{32}$$^{29}$) | 1.00 |
| methyl paraben | 0.25 |
| witch hazel extract | 50.00 |
| purified water | 18.00 |
| | 100.00 |

EXAMPLE 11

| | %/w/w |
|---|---|
| hydrocortisone, U.S.P. | 5.00 |
| methyl paraben | 0.25 |
| dimethyl isosorbide | 15.00 |
| isopropyl alcohol | 15.00 |
| Miranol C2M-SF Conc. | 0.25 |
| polyvinylpyrrolidone (K$_{32}$$^{29}$) | 1.00 |
| witch hazel extract | 50.00 |
| purified water | 18.00 |
| | 100.00 |

EXAMPLE 12

| | %/w/w |
|---|---|
| hydrocortisone, U.S.P. | 5.00 |
| methyl paraben | 0.25 |
| dimethyl isosorbide | 25.00 |
| isopropyl alcohol | 5.00 |
| Miranol C2M-SF Conc. | 0.25 |
| polyvinylpyrrolidone (K$_{32}$$^{29}$) | 1.00 |
| witch hazel extract | 50.00 |
| purified water | 18.00 |

-continued

| | %/w/w |
|---|---|
| | 100.00 |

What is claimed is:

1. A topical formulation for treating the symptoms of hemorrhoids comprising a therapeutically effective amount of hydrocortisone in a liquid solution comprising 0.1–0.25 percent by weight of a fungicide-bactericide; 0.075–1.375 percent by weight of a polymeric film-former; 0.5–15 percent by weight of an alcohol; 0.5–25 percent by weight of dimethyl isosorbide; 0.1–0.25 percent by weight of an amphoteric surfactant; 43.0–58.45 percent by weight of hamamelis extract; and a quantity of water sufficient to make a 100% solution.

2. The topical formulation of claim 1 which comprises a therapeutically effective amount of hydrocortisone in a liquid solution comprising 0.1–0.25 percent by weight of a fungicide-bactericide selected from methyl paraben, propyl paraben, butyl paraben, benzalkonium chloride, cetyl pyridinium chloride, phenyl mercuric chloride, phenol and resorcinol; 0.075–1.375 percent by weight of a polymeric film-former selected from polyvinylpyrrolidone, polymer JR-400, polyvinyl alcohol and sodium carboxymethyl cellulose; 0.5–15 percent by weight of an alcohol selected from propylene glycol, polyethylene glycol-400, isopropyl alcohol and ethyl alcohol; 0.5–25 percent by weight of dimethyl isosorbide; 0.1–0.25 percent by weight of an amphoteric surfactant selected from Miranol C2M-SF Conc., Miranol 2MCA modified, Miranol CM Conc., Miranol MHT; Mirataine CB, Mirataine BB and Mirataine CDMB; 43.0–58.45 percent by weight of hamamelis extract; and a quantity of water to make a 100% solution.

3. The formulation of claim 2 wherein the hydrocortisone is present in an amount between 0.001 and 0.50 percent by weight.

4. The formulation of claim 2 wherein the fungicide-bactericide is methyl paraben.

5. The formulation of claim 2 wherein the polymeric film-former is polyvinylpyrrolidone.

6. The formulation of claim 2 wherein the alcohol is propylene glycol.

7. The formulation of claim 2 wherein the amphoteric surfactant is Miranol C2M-SF Conc.

8. The topical formulation of claim 1 which comprises 0.50 percent by weight of hydrocortisone in a liquid solution comprising 0.25 percent by weight of a fungicide-bactericide selected from methyl paraben, propyl paraben, butyl paraben, benzalkonium chloride, cetyl pyridinium chloride, phenyl mercuric chloride, phenol and resorcinol; 1.0 percent by weight of a polymeric film-former selected from polyvinylpyrrolidone, polymer JR-400, polyvinyl alcohol and sodium carboxymethyl cellulose; 15.0 percent by weight of an alcohol selected from prolylene glycol, polyethylene glycol-400, isopropyl alcohol and ethyl alcohol; 15.0 percent by weight of dimethyl isosorbide; 0.25 percent by weight of an amphoteric surfactant selected from Miranol C2M-SF Conc., Miranol 2MCA modified, Miranol CM Conc., Miranol MHT, Mirataine CB, Mirataine BB and Mirataine CDMB; 50.0 percent by weight of hamamelis extract; and a quantity of water to make a 100% solution.

9. The topical formulation of claim 8 wherein the formulation contains 0.50 percent by weight of hydrocortisone in a liquid solution comprising 0.25 percent by weight of methyl paraben; 1.0 percent by weight of polyvinylpyrrolidone; 15.0 percent by weight of propylene glycol; 15.0 percent by weight of dimethyl isosorbide; 0.25 percent by weight of Miranol C2M-SF Conc., 50.0 percent by weight of hamamelis extract and 18.0 percent by weight of water.

10. The topical formulation of claims 1 or 8 wherein the solution is absorbed on a nonwoven cloth material.

11. A method of treating the symptoms of hemorrhoids which comprises applying to the affected area a topical formulation of claim 1 comprising a therapeutically effective amount of hydrocortisone in a liquid solution consisting of 0.1–0.25 percent by weight of a fungicide-bactericide; 0.075–1.375 percent by weight of a polymeric film-former; 0.5–15 percent by weight of an alcohol; 0.5–25 percent by weight of dimethyl isosorbide; 0.1–0.25 percent by weight of an amphoteric surfactant; 43.0–58.45 percent by weight of hamamelis extract; and a quantity of water sufficient to make a 100% solution.

12. The method of claim 11 wherein the hydrocortisone is present in an amount between 0.001 and 0.50 percent by weight.

13. The method of claim 11 wherein the fungicide-bactericide is selected from methyl paraben, propyl paraben, butyl paraben, benzalkonium chloride, cetyl pyridinium chloride, phenyl mercuric chloride, phenol and resorcinol.

14. The method of claim 11 wherein the fungicide-bactericide is methyl paraben.

15. The method of claim 11 wherein the polymeric film-former is selected from polyvinylpyrrolidone, polymer JR-400, polyvinyl alcohol and sodium carboxymethyl cellulose.

16. The method of claim 11 wherein the amphoteric surfactant is selected from Miranol C2M-SF Conc., Miranol 2MCA modified, Miranol CM Conc., Miranol MHT, Mirataine CB, Mirataine BB and Mirataine CDMB.

17. The method of claim 11 wherein the amphoteric surfactant is Miranol C2M-SF Conc.

18. The method of claim 11 wherein the polymeric film-former is polyvinylpyrrolidone.

19. The method of claim 11 wherein the alcohol is selected from propylene glycol, polyethylene glycol-400, ethyl alcohol and isopropyl alcohol.

20. The method of claim 11 wherein the alcohol is propylene glycol.

21. The method of claim 11 wherein the formulation contains 0.50 percent by weight of hydrocortisone in a liquid solution comprising 0.25 percent by weight of methyl paraben; 1.0 percent by weight of polyvinylpyrrolidone; 15.0 percent by weight of propylene glycol; 15.0 percent by weight of dimethyl isosorbide; 0.25 percent by weight of Miranol C2M-SF Conc.; 50.0 percent by weight of hamamelis extract and 18.0 percent by weight of water.

* * * * *